(12) United States Patent
Linz et al.

(10) Patent No.: US 6,756,508 B2
(45) Date of Patent: Jun. 29, 2004

(54) CINNAMIC ACID SALTS, PROCESSES FOR THEIR PREPARATION, AND THEIR USE AS MEDICAMENTS

(75) Inventors: Guenter Linz, Mittelbiberach (DE); Rainer Soyka, Biberach (DE)

(73) Assignee: Boehringer Ingelheim Pharma GmbH & Co. KG, Ingelheim (DE)

(*) Notice: Subject to any disclaimer, the term of this patent is extended or adjusted under 35 U.S.C. 154(b) by 0 days.

(21) Appl. No.: 10/365,796

(22) Filed: Feb. 13, 2003

(65) Prior Publication Data

US 2003/0166722 A1 Sep. 4, 2003

Related U.S. Application Data

(60) Provisional application No. 60/386,170, filed on Jun. 5, 2002, and provisional application No. 60/387,060, filed on Jun. 7, 2002.

(30) Foreign Application Priority Data

Mar. 4, 2002 (DE) .......................................... 102 09 243
Apr. 12, 2002 (DE) .......................................... 102 16 124

(51) Int. Cl.[7] ...................... C07C 215/28; A61K 31/192
(52) U.S. Cl. ...................... 562/405; 562/471; 562/492; 562/495; 564/353; 514/650; 514/651
(58) Field of Search ............................... 514/650, 651; 562/405, 471, 492, 495; 564/353; 560/405, 471, 492, 495

(56) References Cited

U.S. PATENT DOCUMENTS

| | | | | |
|---|---|---|---|---|
| 4,992,474 A | * | 2/1991 | Skidmore et al. | 514/653 |
| 5,091,422 A | * | 2/1992 | Skidmore et al. | 514/653 |
| 5,126,375 A | * | 6/1992 | Skidmore et al. | 514/651 |
| 5,225,445 A | * | 7/1993 | Skidmore et al. | 514/651 |
| 5,243,076 A | * | 9/1993 | Skidmore et al. | 564/346 |
| 2003/0130300 A1 | * | 7/2003 | Linz et al. | 514/291 |

FOREIGN PATENT DOCUMENTS

DE        34 14 752        10/1984

OTHER PUBLICATIONS

Rees, P.J., Bronchodilators in the Therapy of Chronic Obstructive Pulmonary Disease, Euro. Respir Mon. 1998, 7, 135–148.

Chemical Abstract for DE 3414752 A1, 1984.

Bozung, K–H. et al; "Medicament Compositions Containing Anticholinergically–Effective Compounds And Salmeterol"; US Patent Pub. No. 2002/0115681 A1; Aug. 22, 2002.

Linz, G. et al; "Salicylic Acid Salts Of Salmeterol"; US Patent Pub. No. 2003/0069310 A1; Apr. 10, 2003.

* cited by examiner

*Primary Examiner*—Brian Davis
(74) *Attorney, Agent, or Firm*—Robert P. Raymond; Timothy X. Witkowski; Anthony P. Bottino

(57) ABSTRACT

The present invention relates to new cinnamic acid salts of salmeterol, processes for the preparation thereof as well as the use thereof as pharmaceutical compositions.

6 Claims, No Drawings

CINNAMIC ACID SALTS, PROCESSES FOR THEIR PREPARATION, AND THEIR USE AS MEDICAMENTS

RELATED APPLICATIONS

Benefit of U.S. Provisional Application Serial No. 60/386,170, filed on Jun. 5, 2002, and U.S. Provisional Application Serial No. 60/387,060, filed on Jun. 7, 2002 are hereby claimed.

FIELD OF THE INVENTION

The present invention relates to new cinnamic acid salts of salmeterol, processes for the preparation thereof as well as the use thereof as pharmaceutical compositions.

DETAILED DESCRIPTION OF THE INVENTION

The aim of the present invention is to prepare salts of salmeterol which are characterised by being very well tolerated locally, particularly when administered by inhalation.

This aim is achieved by means of the following cinnamic acid salts of formula 1.

Accordingly the present invention relates to salts of general formula 1

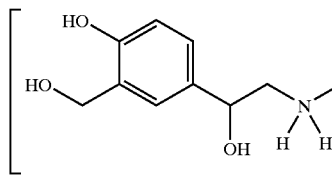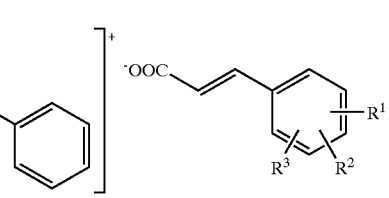

wherein $R^1$ and $R^2$ which may be identical or different denote hydrogen, $C_1$–$C_4$-alkyl, $C_1$–$C_4$-alkoxy, halogen, —$CF_3$ or phenyl
or
if $R^1$ and $R^2$ are adjacent, together they represent a —CH=CH—CH=CH— bridge;
$R^3$ represents hydrogen, $C_1$–$C_4$-alkyl, $C_1$–$C_4$-alkoxy, halogen or —$CF_3$, optionally in the form of the enantiomers thereof, mixtures of the enantiomers or racemates thereof.

Preferred salts of formula 1 are those wherein $R^1$ and $R^2$ which may be identical or different denote hydrogen, methyl, ethyl, propyl, butyl, methoxy, fluorine, chlorine, bromine, —$CF_3$ or phenyl,
or
if $R^1$ and $R^2$ are adjacent, together they represent a —CH=CH—CH=CH— bridge;
$R^3$ represents hydrogen, methyl, ethyl, methoxy, fluorine, chlorine, bromine or —$CF_3$, preferably hydrogen or fluorine, optionally in the form of the enantiomers thereof, mixtures of the enantiomers or racemates thereof.

Particularly preferred are salts of formula 1 wherein $R^1$ and $R^2$ which may be identical or different denote hydrogen, fluorine, chlorine, —$CF_3$
or phenyl
$R^3$ denotes hydrogen or fluorine, preferably hydrogen, optionally in the form of the enantiomers thereof, mixtures of the enantiomers or racemates thereof.

Of particular importance according to the invention are compounds of formula 1, wherein $R^1$ denotes hydrogen;
$R^2$ denotes —$CF_3$ or phenyl;
$R^3$ denotes hydrogen, optionally in the form of the enantiomers thereof, mixtures of the enantiomers or racemates thereof.

Also particularly important are compounds of formula 1 wherein $R^1$ and $R^2$ denotes chlorine;
$R^3$ denotes hydrogen, optionally in the form of the enantiomers thereof, mixtures of the enantiomers or racemates thereof.

The alkyl groups used, unless otherwise stated, are branched and unbranched alkyl groups having 1 to 4 carbon atoms. Examples include: methyl, ethyl, propyl or butyl. The groups methyl, ethyl, propyl or butyl may optionally also be referred to by the abbreviations Me, Et, Prop or Bu. Unless otherwise stated, the definitions propyl and butyl also include all possible isomeric forms of the groups in question. Thus, for example, propyl includes n-propyl and iso-propyl, butyl includes iso-butyl, sec. butyl and tert.-butyl, etc.

The alkyloxy groups used, unless otherwise stated, are branched and unbranched alkyl groups with 1 to 4 carbon atoms which are linked via an oxygen atom. The following may be mentioned, for example: methyloxy, ethyloxy, propyloxy or butyloxy. The groups methyloxy, ethyloxy, propyloxy or butyloxy may optionally also be referred to by the abbreviations MeO, EtO, PropO or BuO. Unless otherwise stated, the definitions propyloxy and butyloxy also include all possible isomeric forms of the groups in question. Thus, for example, propyloxy includes n-propyloxy and iso-propyloxy, butyloxy includes iso-butyloxy, sec. butyloxy and tert.-butyloxy, etc. The word alkoxy may also possibly be used within the scope of the present invention instead of the word alkyloxy. The groups methyloxy, ethyloxy, propyloxy or butyloxy may optionally also be referred to as methoxy, ethoxy, propoxy or butoxy.

Within the scope of the present invention halogen denotes fluorine, chlorine, bromine or iodine. Unless otherwise stated, fluorine and bromine are the preferred halogens. The group CO denotes a carbonyl group.

The salts of formula 1 are new acid addition salts of salmeterol, which is known from the prior art. Salmeterol has a chiral centre. The present invention relates to the salts of formula 1 in racemic or enantiomerically pure form. Both the (R)- and the (S)-enantiomer are of particular importance. Moreover the present invention relates to salts of formula 1 in the form of the non-racemic mixtures of the two enantiomers.

In the compounds of general formula 1 the groups $R^1$, $R^2$ and $R^3$, if they do not represent hydrogen, may each be in the ortho, meta or para position relative to the linking to the ethylene bridge. If none of the groups $R^1$, $R^2$ and $R^3$ denotes hydrogen, the group $R^3$ is preferably linked in the para position and the groups $R^1$ and $R^2$ are linked in the ortho and/or meta position. If one of the groups $R^1$, $R^2$ and $R^3$ denotes hydrogen, preferably at least one of the other groups is linked in the meta or para position, most preferably in the para position. If none of the groups $R^1$, $R^2$ and $R^3$ denotes hydrogen, compounds of general formula 1 wherein the groups $R^1$, $R^2$ and $R^3$ have the same meaning are particularly preferred according to the invention.

The salts 1 according to the invention may be prepared starting from the free base of salmeterol analogously to processes known in the art for forming acid addition salts from secondary amines.

This preparation comprises reacting the free base salmeterol with carboxylic acids of formula 2

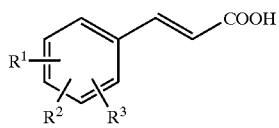

2 wherein the groups $R^1$, $R^2$ and $R^3$ may be defined as hereinbefore, in suitable solvents, preferably organic solvents.

For this purpose the acid 2 is taken up in a suitable solvent, preferably an organic solvent, most preferably a solvent selected from among ethyl acetate, methanol, ethanol, iso-propanol and diethylether or mixtures thereof. If desired the abovementioned solvents may also be used in admixture with tert.-butylmethylether or cyclohexane. The acids 2 taken up in one of the abovementioned solvents are optionally dissolved with heating, preferably to the boiling temperature of the solvent. Salmeterol, optionally dissolved in one of the abovementioned solvents, is added to this solution. The salts 1 are crystallised and isolated from the resulting solution, optionally with cooling.

As has been found, the compounds of general formula 1 are characterised by their range of uses in the therapeutic field. Particular mention should be made of those applications for which the compounds of formula 1 according to the invention may preferably be used on the basis of their pharmaceutical activity as betamimetics.

These include, for example, the treatment of bronchial asthma (normally irritation-induced attacks of bronchial spasm with swelling of the mucosa and increased production of mucus), the treatment of COPD (chronic obstructive bronchitis), the inhibition of premature labour and threatened miscarriage in midwifery (tocolysis), the restoration of the sinus rhythm in the heart in cases of atrio-ventricular block as well as the correcting of bradycardiac heart rhythm disorders (antiarrhythmic agent), the treatment of circulatory shock (vasodilatation and increasing the heart-time volume) as well as the treatment of itching and skin inflammation. The salts of formula 1 are preferably used in the treatment of asthma or COPD.

The salts of general formula 1 may be used on their own or in conjunction with other active substances. These may be, in particular, anticholinergics, antiallergics, leukotriene antagonists, dopamine agonists, PDEIV inhibitors and corticosteroids as well as combinations of active substances.

Examples of anticholinergics which may be mentioned include ipratropium bromide, oxitropium bromide and particularly tiotropium bromide. Drug combinations which contain tiotropium bromide as an additional active substance as well as the compound of formula 1 according to the invention are particularly preferred according to the invention. Combinations which contain, in addition to the compound of formula 1, crystalline tiotropium bromide monohydrate which may be obtained by the experimental procedure described in the experimental section are of particular importance.

This combination is particularly important in the treatment of asthma or COPD, particularly COPD.

Within the scope of the present invention, the corticosteroids which may optionally be used in conjunction with the compound of formula 1 may be compounds selected from among flunisolide, beclomethasone, triamcinolone, budesonide, fluticasone, mometasone, ciclesonide, rofleponide and dexamethasone. Preferably, within the scope of the present invention, the corticosteroids are selected from among flunisolide, beclomethasone, triamcinolone, budesonide, fluticasone, mometasone, ciclesonide and dexamethasone, while budesonide, fluticasone, mometasone and ciclesonide are important and budesonide and fluticasone are particularly important. In some cases, within the scope of the present patent application, the term steroids is used on its own instead of the word corticosteroids. Any reference to steroids within the scope of the present invention includes a reference to salts or derivatives which may be formed from the steroids. Examples of possible salts or derivatives include: sodium salts, sulphobenzoates, phosphates, isonicotinates, acetates, propionates, dihydrogen phosphates, palmitates, pivalates or furoates. In some cases the corticosteroids may also occur in the form of their hydrates.

Within the scope of the present invention, the term dopamine agonists, which may optionally be used in conjunction with the compound of formula 1, denotes compounds selected from among bromocriptine, cabergolin, alpha-dihydroergocryptine, lisuride, pergolide, pramipexol, roxindol, ropinirol, talipexol, tergurid and viozan. It is preferable within the scope of the present invention to use, as combination partners with the compound of formula 1, dopamine agonists selected from among pramipexol, talipexol and viozan, pramipexol being of particular importance. Any reference to the abovementioned dopamine agonists also includes, within the scope of the present invention, a reference to any pharmacologically acceptable acid addition salts and hydrates thereof which may exist. By the physiologically acceptable acid addition salts thereof which may be formed by the abovementioned dopamine agonists are meant, for example, pharmaceutically acceptable salts selected from among the salts of hydrochloric acid, hydrobromic acid, sulphuric acid, phosphoric acid, methanesulphonic acid, acetic acid, fumaric acid, succinic acid, lactic acid, citric acid, tartaric acid and maleic acid.

Examples of antiallergic agents which may be used according to the invention as a combination with the compound of formula 1 include epinastin, cetirizin, azelastin, fexofenadin, levocabastin, loratadine, mizolastin, ketotifen, emedastin, dimetinden, clemastine, bamipin, cexchloropheniramine, pheniramine, doxylamine, chlorophenoxamine, dimenhydrinate, diphenhydramine, promethazine, ebastin, desloratidine and meclizine. Preferred antiallergic agents which may be used within the scope of the present invention in combination with the compounds of formula 1 according to the invention are selected from among epinastin, cetirizin, azelastin, fexofenadin, levocabastin, loratadine, ebastin, desloratidine and mizolastin, epinastin and desloratidine being particularly preferred. Any reference to the abovementioned antiallergic agents also includes, within the scope of the present invention, a reference to any pharmacologically acceptable acid addition salts thereof which may exist.

Examples of PDE-IV inhibitors which may be used according to the invention as a combination with the compound of formula 1 include compounds selected from among enprofylline, roflumilast, ariflo, Bay-198004, CP-325,366, BY343, D-4396 (Sch-351591), V-11294A and AWD-12-281. Preferred PDE-IV inhibitors are selected from among enprofylline, roflumilast, ariflo and AWD-12-281. Any reference to the abovementioned PDE-IV inhibitors also includes, within the scope of the present invention, a reference to any pharmacologically acceptable acid addition salts thereof which may exist. By the physiologically acceptable acid addition salts which may be formed by the abovementioned PDE-IV inhibitors are meant, for example, pharmaceutically acceptable salts selected from among the salts of hydrochloric acid, hydrobromic acid, sulphuric acid, phosphoric acid, methanesulphonic acid, acetic acid, fumaric acid, succinic acid, lactic acid, citric acid, tartaric acid and maleic acid. According to the invention, the salts selected from among the acetate, hydrochloride, hydrobromide, sulphate, phosphate and methanesulphonate are preferred.

Suitable preparations for administering the salts of formula 1 include for example tablets, capsules, suppositories and powders, etc. The content of the pharmaceutically active compound(s) should be in the range from 0.05 to 90 wt.-%, preferably 0.1 to 50 wt.-% of the composition as a whole. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number or layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered by the usual methods, preferably by inhalation in the treatment of asthma or COPD.

For inhalation the compounds may be in the form of inhalable powders, propellant-containing inhalable solutions or suspensions or propellant-free inhalable solutions or suspensions.

The inhalable powders which may be used and are preferred within the scope of the invention may contain the salts 1 either on their own or in admixture with suitable physiologically acceptable excipients. If the salts 1 are present in admixture with physiologically acceptable excipients, the following physiologically acceptable excipients may be used to prepare these inhalable powders according to the invention: monosaccharides (e.g. glucose or arabinose), disaccharides (e.g. lactose, saccharose, maltose), oligo- and polysaccharides (e.g. dextrane), polyalcohols (e.g. sorbitol, mannitol, xylitol), salts (e.g. sodium chloride, calcium carbonate) or mixtures of these excipients with one another. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred.

The inhalation aerosols containing propellant gas which may be used according to the invention may contain the salts 1 dissolved in the propellant gas or in dispersed form. The propellant gases which may be used to prepare the inhalation aerosols are known from the prior art. Suitable propellant gases are selected from among hydrocarbons such as n-propane, n-butane or isobutane and halohydrocarbons such as preferably fluorinated derivatives of methane, ethane, propane, butane, cyclopropane or cyclobutane. The propellant gases mentioned above may be used on their own or in mixtures thereof. Particularly preferred propellant gases are fluorinated alkane derivatives selected from TG134a (1,1,1,2-tetrafluoroethane), TG227 (1,1,1,2,3,3,3-heptafluoropropane) and mixtures thereof.

The propellant-driven inhalation aerosols which may be used according to the invention may also contain other ingredients such as co-solvents, stabilisers, surfactants, antioxidants, lubricants and pH adjusters. All these ingredients are known in the art.

If the salts 1 according to the invention are administered in the form of propellant-free inhalable solutions and suspensions, the solvent used may be an aqueous or alcoholic, preferably an ethanolic solution. The solvent may be water on its own or a mixture of water and ethanol. The relative proportion of ethanol compared with water is not limited but the maximum is up to 70 percent by volume, more particularly up to 60 percent by volume and most preferably up to 30 percent by volume. The remainder of the volume is made up of water. The solutions or suspensions containing 1 are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Preferred inorganic acids are hydrochloric and sulphuric acids. Of the organic acids, ascorbic acid, fumaric acid and citric acid are preferred. If desired, mixtures of the above acids may be used, particularly in the case of acids which have other properties in addition to their acidifying qualities, e.g. as flavourings, antioxidants or complexing agents, such as citric acid or ascorbic acid, for example. According to the invention, it is particularly preferred to use hydrochloric acid to adjust the pH.

For oral administration the tablets may, of course contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

The dosage of the compounds according to the invention is naturally highly dependent on the method of administration and the complaint which is being treated. When administered by inhalation the compounds of formula 1 are characterised by a high potency even at doses in the µg range. The compounds of formula 1 may also be used effectively above the µg range. The dosage may then be in the gram range, for example.

The example of synthesis described below serves to illustrate the present invention still further. However, it is to be regarded as only an example of a procedure, illustrating one possible method of obtaining the compound according to the invention, without restricting the invention to the object described below by way of example.

EXAMPLES OF SYNTHESIS 4-hydroxy-α$^1$-[[[6-(4-phenylbutoxy)-hexyl]-amino]-methyl]-1,3-benzenedimethanol-4-phenylcinnamate salt 1a:

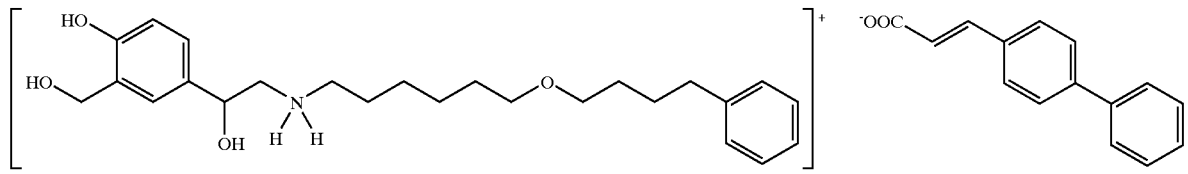

1.35 g (6 mmol) of 4-phenylcinnamic acid is dissolved in 75 mL of ethyl acetate while refluxing. To this solution is added a warm solution of 2.5 g (6 mmol) of salmeterol in 25 mL of ethyl acetate. The solution is left to cool and stirred for 16 h at ambient temperature. The suspension is filtered, the precipitate is washed with ethyl acetate and tert.-butylmethyl ether and dried in vacuo at 25–30° C. 3.47 g of the title compound are obtained as a colourless solid. Melting point: 109° C.;

The following compounds were prepared analogously:

4-hydroxy-α$^1$-[[[6-(4-phenylbutoxy)-hexyl]-amino]-methyl]-1,3-benzenedimethanol-4-trifluoromethyl-cinnamate salt 1b;

melting point: 125° C.;

4-hydroxy-α$^1$-[[[6-(4-phenylbutoxy)-hexyl]-amino]-methyl]-1,3-benzenedimethanol -3,4-dichloro-cinnamate salt 1c;

melting point: 116° C.;

4-hydroxy-α$^1$-[[[6-(4-phenylbutoxy)-hexyl]-amino]-methyl]-1,3-benzenedimethanol-2,4-dichloro-cinnamate salt 1d;

melting point: 183° C.;

4-hydroxy-α$^1$-[[[6-(4-phenylbutoxy)-hexyl]-amino]-methyl]-1,3-benzenedimethanol-cinnamate salt 1e;

melting point: 89° C.;

4-hydroxy-α$^1$-[[[6-(4-phenylbutoxy)-hexyl]-amino]-methyl]-1,3-benzenedimetbanol-3-(2-naphthyl) acrylate salt 1f;

melting point: 97° C.;

4-hydroxy-α$^1$-[[[6-(4-phenylbutoxy)-hexyl]-amino]-methyl]-1,3-benzenedimethanol-3-(1-naphthyl) acrylate salt 1g;

melting point: 77° C.;

4-hydroxy-α$^1$-[[[6-(4-phenylbutoxy)-hexyl]-amino]-methyl]-1,3-benzenedimethanol-2,6-dichloro-cinnamate salt 1h;

melting point: 82° C.;

4-hydroxy-α$^1$-[[[6-(4-phenylbutoxy)-hexyl]-amino]-methyl]-1,3-benzenedimethanol-2,5-dimethoxy-cinnamate salt 1i;

melting point: 88° C.;

4-hydroxy-α$^1$-[[[6-(4-phenylbutoxy)-hexyl]-amino]-methyl]-1,3-benzenedimethanol-2-trifluoromethyl-cinnamate salt 1j;

melting point: 94° C.;

4-hydroxy-α$^1$-[[[6-(4-phenylbutoxy)-hexyl]-amino]-methyl]-1,3-benzenedimethanol-3-trifluoromethyl-cinnamate salt 1k;

melting point: 92° C.;

4-hydroxy-α$^1$-[[[6-(4-phenylbutoxy)-hexyl]-amino]-methyl]-1,3-benzenedimethanol-3-chloro-cinnamate salt 1l;

melting point: 90° C.;

4-hydroxy-α$^1$-[[[6-(4-phenylbutoxy)-hexyl]-amino]-methyl]-1,3-benzenedimethanol-4-bromo-cinnamate salt 1m;

melting point: 127° C.;

4-hydroxy-α$^1$-[[[6-(4-phenylbutoxy)-hexyl]-amino]-methyl]-1,3-benzenedimethanol-4-chloro-cinnamate salt 1n;

melting point: 123° C.; 7

4-hydroxy-α$^1$-[[[6-(4-phenylbutoxy)-hexyl]-amino]-methyl]-1,3-benzenedimethanol-4-methoxy-cinnamate salt 1o;

melting point: 98° C.;

4-hydroxy-α$^1$-[[[6-(4-phenylbutoxy)-hexyl]-amino]-methyl]-1,3-benzenedimethanol-4-fluoro-cinnamate salt 1p;

melting point: 113° C.;

4-hydroxy-α$^1$-[[[6-(4-phenylbutoxy)-hexyl]-amino]-methyl]-1,3-benzenedimethanol-4-isopropyl-cinnamate salt 1q;

melting point: 82° C.;

4-hydroxy-α$^1$-[[[6-(4-phenylbutoxy)-hexyl]-amino]-methyl]-1,3-benzenedimethanol-4-tert-butyl-cinnamate salt 1r;

melting point: 93° C.;

4-hydroxy-α$^1$-[[[6-(4-phenylbutoxy)-hexyl]-amino]-methyl]-1,3-benzenedimethanol-2,4-difluoro-cinnamate salt 1s;

melting point: 121° C.;

4-hydroxy-α$^1$-[[[6-(4-phenylbutoxy)-hexyl]-amino]-methyl]-1,3-benzenedimethanol-3,4-difluoro-cinnamate salt 1t;

melting point: 102° C.;

4-hydroxy-α$^1$-[[[6-(4-phenylbutoxy)-hexyl]-amino]-methyl]-1,3-benzenedimethanol-2,4,5-trifluoro-cinnamate salt 1u;

melting point: 120° C.;

4-hydroxy-α$^1$-[[[6-(4-phenylbutoxy)-hexyl]-amino]-methyl]-1,3-benzenedimethanol-3,4,5-trifluoro-cinnamate salt 1v;

melting point: 107° C.;

In the abovementioned salts 1 according to the invention the base salmeterol and the acid of formula 2 are in a molar ratio of salmeterol:acid of 1:1.

The identity of the abovementioned compounds was confirmed by 1H-NMR spectroscopy and ESI mass spectrometry.

The salts of formula 1 according to the invention may optionally be used in combination with for example crystalline tiotropium bromide monohydrate. In so far as the latter is not yet known in the art its preparation is described hereinafter.

Tiotropium bromide may be obtained as described in European Patent Application EP 418 716 A1. Crystalline tiotropium bromide monohydrate may be obtained therefrom by the following method.

In a suitable reaction vessel 15.0 kg of tiotropium bromide are added to 25.7 kg of water. The mixture is heated to 80–90° C. and stirred at constant temperature until a clear solution is formed. Activated charcoal (0.8 kg), moistened with water, is suspended in 4.4 kg of water, this mixture is added to the solution containing tiotropium bromide and rinsed with 4.3 kg of water. The resulting mixture is stirred for at least 15 min at 80–90° C. and then filtered through a heated filter into an apparatus which has been preheated to an outer temperature of 70° C. The filter is rinsed with 8.6 kg of water. The contents of the apparatus are cooled to a temperature of 20–25° C. at a rate of 3–5° C. per 20 minutes. The apparatus is further cooled to 10–15° C. by cold water cooling and the crystallisation is completed by stirring for at least one hour. The crystals are separated off using a suction drier, the isolated crystal slurry is washed with 9 litres of cold water (10–15° C.) and cold acetone (10–15° C.). The crystals obtained are dried at 25° C. for 2 hours in a nitrogen current.

Yield: 13.4 kg of crystalline tiotropium bromide monohydrate (86% of theory).

The following examples of formulations illustrate the present invention without restricting its scope:

EXAMPLES OF PHARMACEUTICAL FORMULATIONS

| A) Tablets | per tablet |
|---|---|
| active substance | 5 mg |
| lactose | 140 mg |
| corn starch | 240 mg |
| polyvinylpyrrolidone | 10 mg |
| magnesium stearate | 5 mg |
| | 400 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) Tablets | per tablet |
|---|---|
| active substance | 10 mg |
| lactose | 55 mg |
| corn starch | 190 mg |
| microcrystalline cellulose | 35 mg |
| polyvinylpyrrolidone | 15 mg |
| sodium-carboxymethyl starch | 23 mg |
| magnesium stearate | 2 mg |
| | 330 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodium carboxymethyl starch and the magnesium stearate are added and mixed in and the mixture is compressed to form tablets of a suitable size.

| C) Metering aerosol | | |
|---|---|---|
| active substance | 0.005 | |
| sorbitan trioleate | 0.1 | |
| monofluorotrichloromethane and difluorodichloromethane | 2:3 | ad 100 |

The percentages specified are percent by weight. The suspension is transferred into a conventional aerosol container with a metering valve. Preferably, 50 µl of suspension are delivered per spray. The active substance can also be in a higher dose if desired (e.g. 0.02 wt.-%).

| D) Inhalable Powder | |
|---|---|
| active substance | 110 µg |
| lactose monohydrate | ad 25 mg |

The inhalable powder is prepared in the usual way by mixing the individual ingredients together.

| E) Inhalable powder | |
|---|---|
| active substance | 50 µg |
| tiotropium bromide monohydrate | 22.5 µg |
| lactose monohydrate | ad 25 mg |

The inhalable powder is prepared in the usual way by mixing the individual ingredients together.

What is claimed is:

1. A compound of the formula 1

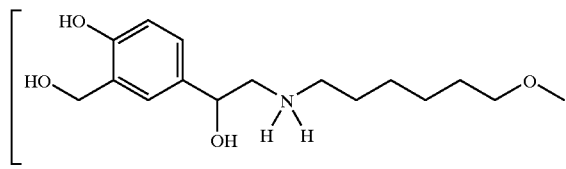

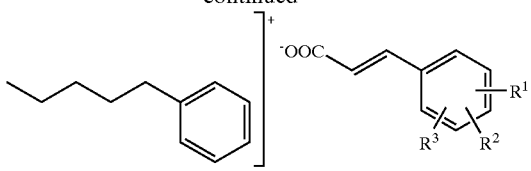

wherein:

$R^1$ and $R^2$, which are identical or different, are each hydrogen, $C_1$–$C_4$-alkyl, $C_1$–$C_4$-alkoxy, halogen, —$CF_3$, or phenyl, or, if $R^1$ and $R^2$ are adjacent, together they are a —CH═CH—CH═CH— bridge; and $R^3$ is hydrogen, $C_1$–$C_4$-alkyl, $C_1$–$C_4$-alkoxy, halogen, or —$CF_3$.

2. The compound of the formula 1 according to claim 1, wherein $R^1$ and $R^2$, which are identical or different, are each hydrogen, methyl, ethyl, propyl, butyl, methoxy, fluorine, chlorine, bromine, —$CF_3$, or phenyl, or, if $R^1$ and $R^2$ are adjacent, together they are a —CH═CH—CH═CH— bridge; and $R^3$ is hydrogen, methyl, ethyl, methoxy, fluorine, chlorine, bromine, or —$CF_3$.

3. The compound of the formula 1 according to claim 1, wherein:

$R^1$ and $R^2$, which are identical or different, are each hydrogen, fluorine, chlorine, —$CF_3$, or phenyl; and $R^3$ is hydrogen or fluorine.

4. The compound of the formula 1 according to claim 1, wherein:

$R^1$ is hydrogen;

$R^2$ is —$CF_3$ or phenyl; and $R^3$ is hydrogen.

5. The compound of the formula 1 according to claim 1, wherein:

$R^1$ and $R^2$ are each chlorine; and $R^3$ is hydrogen.

6. A pharmaceutical composition comprising a compound in accordance with one of claims 1, 2, 3, 4, or 5, and a physiologically acceptable excipient.

* * * * *